United States Patent [19]

Rudt

[11] Patent Number: 5,741,299
[45] Date of Patent: Apr. 21, 1998

[54] PUNCTURE-PROOF SUTURE NEEDLE ASSEMBLY

[76] Inventor: Louis L. Rudt, 1617 Crescent Ridge Rd., Daytona Beach, Fla. 32118

[21] Appl. No.: 811,899

[22] Filed: Mar. 5, 1997

[51] Int. Cl.⁶ ................................................. A61B 17/04
[52] U.S. Cl. ........................................... 606/224; 606/227
[58] Field of Search ................................. 606/222–227

[56] References Cited

U.S. PATENT DOCUMENTS

| | | | |
|---|---|---|---|
| 5,180,385 | 1/1993 | Sontag | 606/224 |
| 5,549,629 | 8/1996 | Thomas et al. | 606/224 |

FOREIGN PATENT DOCUMENTS

| | | | |
|---|---|---|---|
| WO 92/08412 | 5/1992 | WIPO. | |
| 9313714 | 7/1993 | WIPO | 606/148 |

*Primary Examiner*—Gary Jackson
*Attorney, Agent, or Firm*—Richard C. Litman

[57] ABSTRACT

The surgical suturing assembly of the present invention protects a user from accidental puncture wounds. A surgical needle is contained within a rigidly-walled protective casing, having a proximate end defining a first aperture through which the needle is inserted. The casing tapers distally to define a second aperture for passage and limiting protrusion of the sharp tip of the needle. The casing defines a pair of openings near the distal end, through which openings the needle shaft is exposed when the sharp tip extends through the second aperture. Upon insertion of the needle, the casing is plugged by a suture guide that engages the first aperture, the suture guide having an eye for threading onto the suturing thread. When plugged, the suture guide functions to slidingly retain a needle within the casing. In use, a surgeon grasps the suturing needle assembly where the exposed section of the needle shaft contacts the casing. The surgeon then punctures the designated patient biological tissue and extends the distal part of the assembly therethrough. The surgeon then releases the assembly and regrasps the distal casing thereof, pulling the remaining portion of the assembly through the tissue sections. By engaging only the distal casing, the surgeon frees the surgical needle, allowing it to slidably recess into the proximate casing when the suturing needle assembly is pulled completely through the apertures in the tissue, to ultimately obscure the sharp needle tip and effectively prevent accidental self-puncture.

8 Claims, 3 Drawing Sheets

PUNCTURE-PROOF SUTURE NEEDLE ASSEMBLY

BACKGROUND OF THE INVENTION

1. Field of the Invention

The present invention relates to suture needles for use in surgical applications, and more specifically to medical grade suture needles designed to prevent the accidental puncturing of a user's skin.

2. Description of the Prior Art

Recently, the grim repercussions of blood-borne infectious diseases such as hepatitis and AIDS have forced the medical community to better safeguard against contamination resulting from contact with bodily fluids. One example of this current prophylactic awareness involves surgical suture needles, and modifications thereto that aim to protect a user from accidentally puncturing themselves, which in the past has led to the transmission of lethal blood-borne infectious diseases. Unlike other types of medical equipment, the surgical suture needle is small and very sharp. These properties make handling of the needle, even for a skilled surgeon, potentially harmful, exposing the surgeon, as well as other medical personnel, to unintentional skin penetration and its deadly consequences. Accordingly, self-puncture preventative measures are warranted.

The surgical suture needle described in World Intellectual Property Organization Patent WO 92/08412 features a blunt tip. Extensive cadaver research documents the resistance of gloved palmar cutaneous tissues (skin) to needles having tips of different "bluntness" levels, which largely retain their piercing capabilities for puncturing non-cutaneous soft body tissues. However, the constantly exposed needle tip still presents ample opportunities for possible accidental puncture of the user's skin. At the same time, tip bluntness could adversely effect a suture needle's smooth penetration of non-cutaneous tissue. Given the increased surface area of a blunt tip, the surgeon must use more force to puncture non-cutaneous tissues, leading to potential tearing of the suture hole.

Another approach to prevent accidental user puncture involves a protective sheath, as disclosed in U.S. Pat. Nos. 5,180,385 and 5,549,629. U.S. Pat. No. 5,180,385 teaches a suturing assembly comprising a surgical needle having a hump within a casing or sheath having an aperture, wherein the hump of the needle protrudes through the casing aperture. In use, a surgeon deforms the hump of the needle, forcing the sharpened distal point of the needle to project through the distal opening of the casing. After penetrating the tissue with the needle/casing assembly, the surgeon releases the deforming force, causing the needle to return to its original position and leaving an unsharpened point for safe manipulation.

While the hump needle design of the suturing assembly of '385 affords a mechanism by which the sharpened point can be safely recessed into the casing thereof, it also creates problems involving both surgical and manufacturing concerns. The hump of the needle, while protruding only minimally through the aperture in the casing, interrupts the otherwise continuous surface of the assembly, thereby leading to potential tearing of the suture hole. Repeated sutures using the device of '385 could also introduce surgical debris into the recess defined by the hump, obstructing its deformation and ultimately compromising its smooth operation. Furthermore, the hump needle, and the driver designed especially for use with it, would be more expensive to manufacture than existing conventional surgical needles and drivers, which are incompatible with the design of the device of '385.

The protective apparatus of '629 provides for a retractable, telescoping, surgical needle cover and a collapsible needle, such that the sharp tip of the needle is covered after use, thereby protecting the user from accidental self-puncture. Three embodiments of the device are disclosed. In two of the embodiments, the sharp tip of the needle collapsibly retracts upon striking "a hard object," but does not retract when piercing the soft flesh of a patient during surgery. The hardness required for collapsing the needle is not specified, leading one to conclude that if the sharp needle penetrates the soft flesh of a patient, then it can just as easily penetrate the soft flesh of a surgeon's hand or finger, or of the hand or finger of anyone else handling the needle. Thus the mechanism for safely covering the sharp point of the needle is not well controlled nor reliable to prevent the accidental puncturing of a user's skin.

The other embodiment of the device of '629 employs a lever mechanism, movably disposed within a groove formed in the proximate end of the needle, to control movement of the cover over the sharp needle tip. Given the intricate nature of endosurgical suturing, activating this type of lever mechanism could prove difficult and cumbersome, ultimately complicating the procedure. Moreover this embodiment of '629 would also require a needle designed specifically to incorporate the groove and lever mechanism, and would thereby be more expensive to manufacture than existing conventional surgical needles, which are incompatible.

In light of the shortcomings of the above inventions and patents, there is a need for a surgical suturing assembly that securely protects a user from accidental puncture wounds. There is also a need for such a surgical suturing assembly that can utilize existing surgical needles, without necessitating structural modifications thereto. Furthermore, an easily controlled protection mechanism for a surgical suturing assembly is needed, whereby the safety of the user is not compromised.

None of the above inventions and patents, taken either singly or in combination, is seen to describe the instant invention as claimed.

SUMMARY OF THE INVENTION

The surgical suturing assembly of the present invention aims to protects a user from accidental puncture wounds, which have been known to result in the transmission of lethal blood-borne infectious diseases. To best facilitate such protection, the surgical suturing assembly described herein provides a user-controlled cover mechanism for the sharp needle tip. Also, the present invention permits the utilization of existing surgical needles, without necessitating structural modifications thereto.

An open-ended, rigidly walled casing for receiving a surgical or suturing needle is provided, which casing has a curvature accommodating the curvature of a suturing needle and is dimensioned to have a length in excess of the suturing needle such that the needle may be withdrawn into the casing. The proximate end of the casing defines a first aperture through which the needle is inserted. The casing tapers at its distal end and defines a second aperture that both allows the sharp tip of the needle to protrude for use during suturing and limits the protrusion of the tip. The casing comprises interconnecting distal and proximate sections, which are integrally connected by a pair of diametrically opposed flanges. The sections and flanges together define a pair of diametrically opposed openings, through which the surgical needle is exposed for grasping by surgical needle driver, such as a hemostat clamp, for securing the tip in an extended position through the second aperture.

A substantially cylindrical suture guide insertably engages the proximate end of the casing and plugs the first aperture to retain a needle within the casing; the guide further defines an eye through which the suturing medium is threaded. In conventional use, a suturing needle is provided with a suturing medium, such as proline thread, attached through the eye of the needle or affixed to the blunt end of the needle. The suturing medium is passed through the eye of the suture guide, the eye being dimensioned to prevent passage of the needle. When the suture guide is plugged into the first aperture, it forms a stop preventing the needle from escaping the casing, thereby allowing reciprocal movement of the needle within the casing. Thus, the sheath may be grasped by a clamp and slid forward to allow the needle to be retracted and ultimately drawn forward inside the sheath by virtue of the suture guide abutting the eye of the needle. The suture guide can be crimped to further secure the suturing medium therein.

Each component of the suturing needle assembly is manufactured from surgical grade stainless steel, which is corrosion-resistant and can be sterilized before use. The needle itself is a conventional suturing needle, available in a wide array of sizes, shapes and designs. Accordingly, the casing can be manufactured to accommodate any of the known various surgical needle embodiments. While the distal section of the casing tapers to form a snug seal with the needle tip, the proximate section engages the needle relatively loosely, to better facilitate the sliding displacement of thereof. All edges of the casing disposed proximate to the needle are beveled to eliminate discontinuities along the surface of the suturing needle assembly.

In use, a surgeon employs the needle driver to manipulate the suturing needle assembly, grasping the flanges and the exposed section of the needle proximate thereto in the opposing jaws of the driver, thereby securing the needle within the casing. The surgeon can then direct the suturing needle assembly, with the needle tip exposed, to puncture two sections of patient biological tissue to be sutured together. Upon extending the distal casing section through the apertures in the tissue sections, the surgeon disengages the opposing jaws of the driver. The surgeon then repositions the opposing jaws of the driver to grasp the distal casing section, and pulls the remaining portion of the suturing needle assembly through the apertures in the tissue sections. By engaging only the distal casing section, the needle therefrom, so slidably recesses into the proximate casing section when the suturing needle assembly is pulled completely through the apertures in the tissue sections. The "drag" of the suturing medium facilitates the displacement of the needle within the casing. In this orientation, the needle tip is safely sheathed within the proximate casing section, thereby preventing accidental self-puncture.

When preparing to make a second suture, the surgeon inverts the suturing needle assembly to allow the surgical needle to drop into its extended-tip position, whereby the needle tip is exposed for further penetration of patient biological tissue.

Accordingly, it is a principal object of the invention to protect medical personnel from accidental puncture wounds.

It is another object of the invention to incorporate a user-controlled mechanism for encasing the sharp needle tip after penetration of tissue.

It is a further object of the invention to utilize existing surgical needles, without necessitating structural modifications thereto.

Still another object of the invention is to provide a protective device for utilization with standard surgical needle drivers including hemostat clamps and the like.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
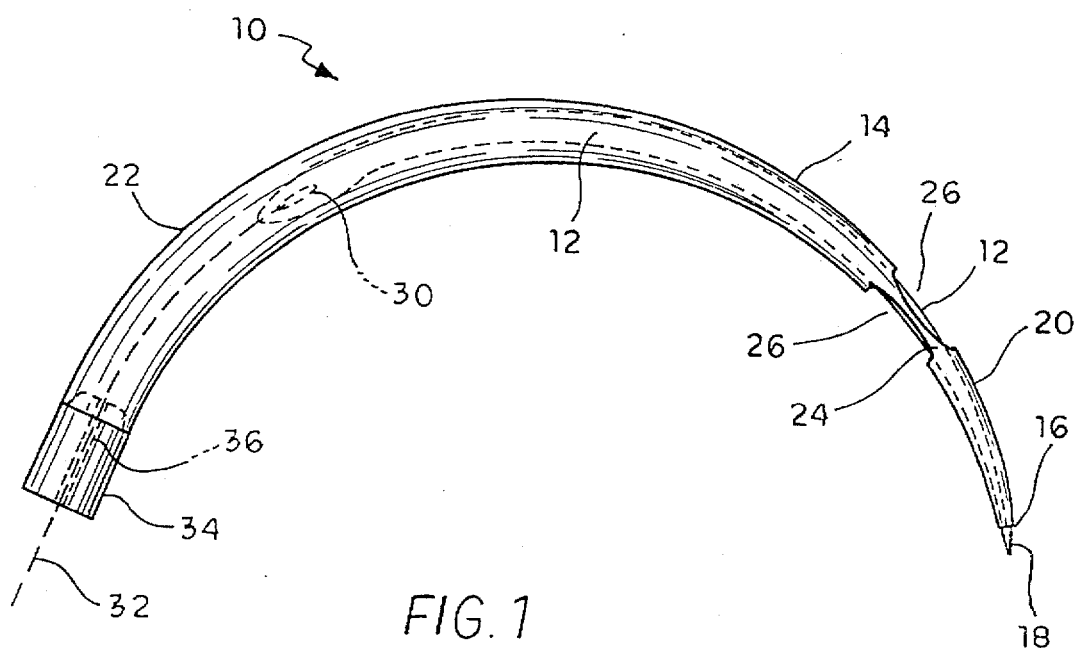
FIG. 1 is a side elevational view of the puncture-proof suturing needle assembly of the present invention, in an open state with the sharp needle tip exposed.

The present invention, referenced as 10 herein, is illustrated in FIG. 1. A surgical needle 12 of well-known design is shown contained within a rigid-walled, substantially frusto-conical casing 14, having a curvature paralleling the surgical needle 12. The proximate end of surgical needle 12 defines an eyelet 30 through which the desired length of chosen suturing medium 32 is threaded in a well-known fashion. The proximate end of casing 14 defines a first aperture 28, through which surgical needle 12 has been inserted into the casing 14. The distal end of casing 14 tapers to define an open-end or second aperture 16, which accommodates protrusion of the sharp tip 18 of surgical needle 12. The aperture is sized in diameter to limit the protrusion of the needle to only the tip 18.

Casing 14 comprises distal and proximate sections 20, 22, each integrally connected to a pair of diametrically opposed flanges 24. Flanges 24 connect the proximate part of section 20 to the distal part of section 22. Together sections 20, 22 and flanges 24 define a pair of diametrically opposed openings 26. The openings are positioned so that the surgical needle 12 is substantially exposed when tip 18 extends through aperture 16 (as shown in FIG. 1); however, the openings are positioned beyond the end of the tip when the needle is fully retracted in a closed state (as shown in FIG. 2).

A substantially cylindrical suture guide 34 insertably plugs aperture 28 after surgical needle 12 is inserted therein. Suture guide 34 defines an eye hole 36 that extends through its substantial center, through which suturing medium 32 is threaded. Suture guide 34 can be crimped to further secure suturing medium 32 therein. The eye hole 36 is dimensioned in diameter to prevent passage of the needle. When the suture guide is plugged into the first aperture, it forms a stop preventing the needle from escaping the casing, thereby allowing reciprocal movement of the needle within the casing.

Figure 2:
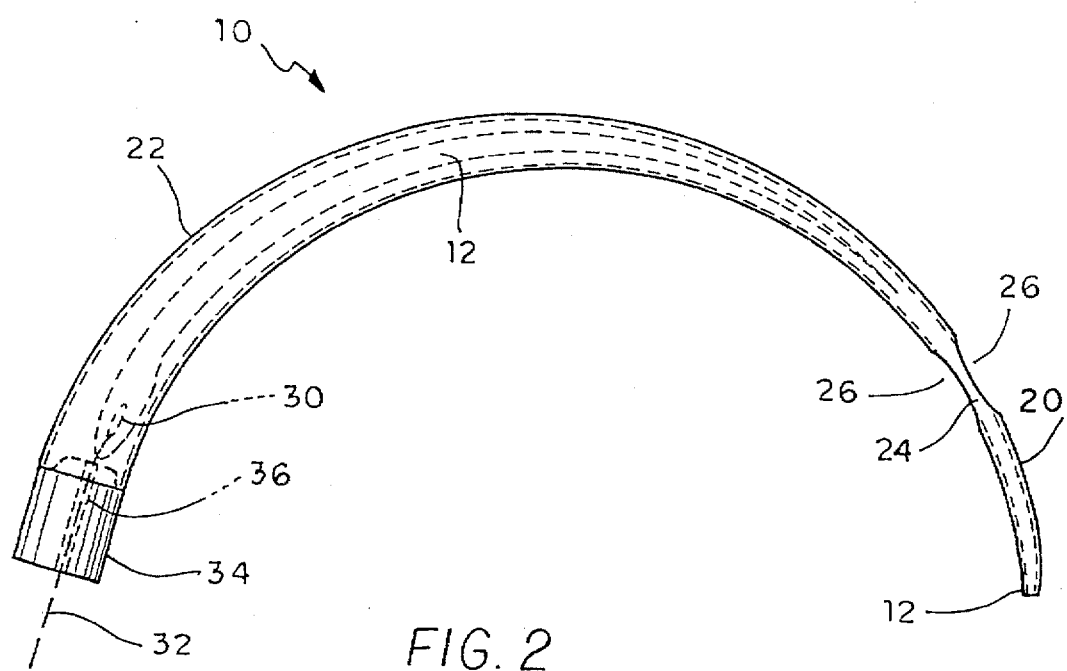
FIG. 2 is a side elevational view of the puncture-proof suturing needle assembly of the present invention, in a closed state with the sharp needle tip recessed.

FIG. 2 illustrates the suturing needle assembly 10 with surgical needle 12 having been slidably displaced so that section 22 of casing 14 contains it completely. Suture guide 34 functions to retain surgical needle 12 in its recessed position within casing 14. In this orientation, needle tip 18 is safely protected within section 22, to prevent accidental self-puncture.

Figure 3:
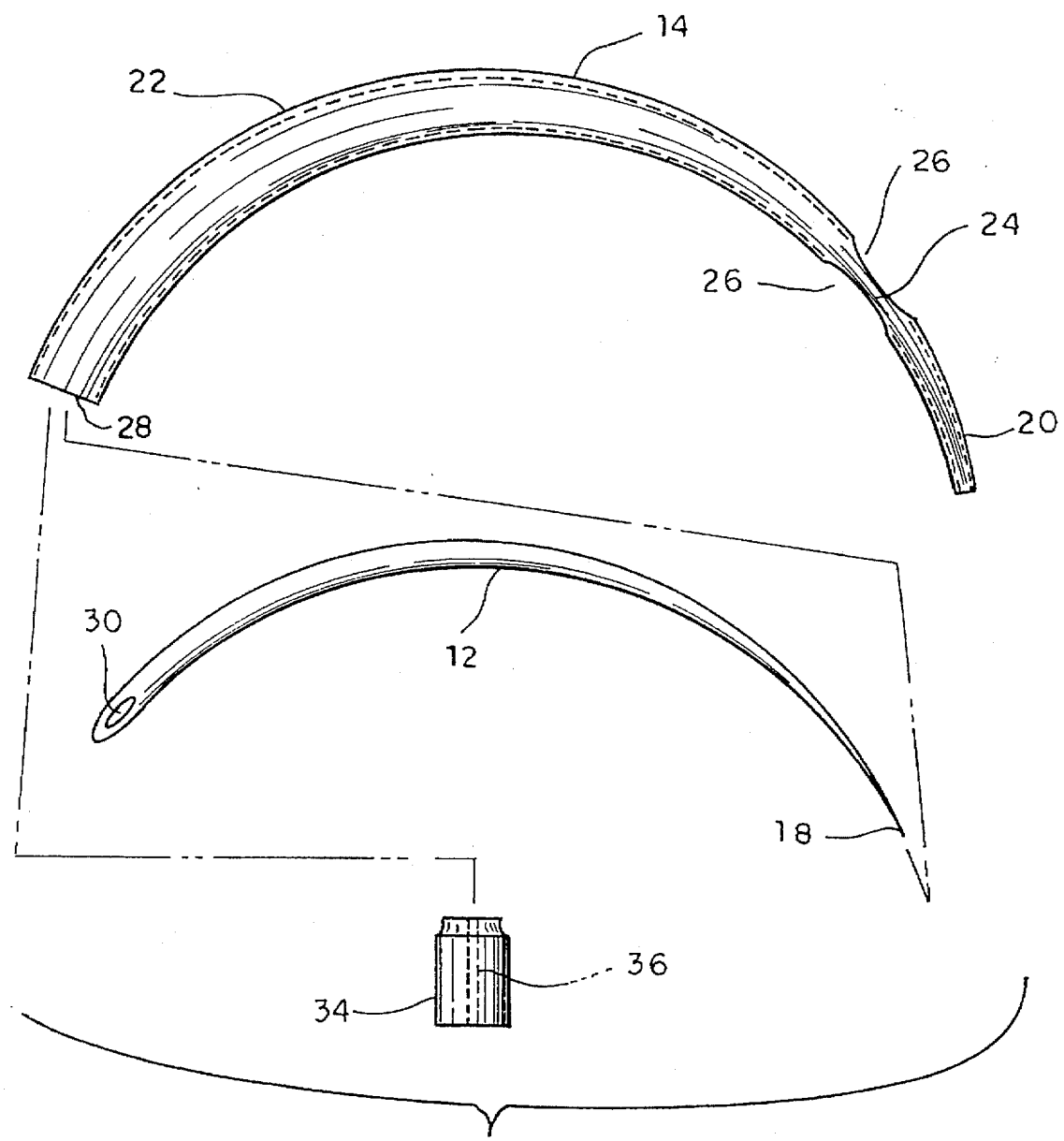
FIG. 3 is an exploded, side elevational view of the components of the puncture-proof suturing needle assembly of the present invention.

Surgical needle 12, casing 14 and suture guide 34 are shown as separate components in FIG. 3. Each of the components is manufactured from surgical grade stainless steel, which is corrosion-resistant and can be sterilized before use. Surgical needle 12 itself is a conventional suturing needle, available in a wide array of sizes, shapes and designs. Accordingly, casing 14 can be manufactured to accommodate any of the known various surgical needle embodiments, but in all cases the casing 14 exceeds the length of the needle to allow positioning of the diametrically opposed openings 26 beyond the end of the needle tip when in a retracted state. Section 20 is tapered to form a snug seal with needle tip 18 at aperture 16, to insure a smooth interface therewith and eliminate discontinuities along the distal part of suturing needle assembly 10. Section 22 engages surgical needle 12 relatively loosely, to better facilitate the sliding displacement of surgical needle 12 therein. The edges of sections 20, 22 and the edges of flanges 24 which define openings 26 are beveled, to insure a smooth interface with surgical needle 12 and eliminate discontinuities along the surface of suturing needle assembly 10.

Figure 4:
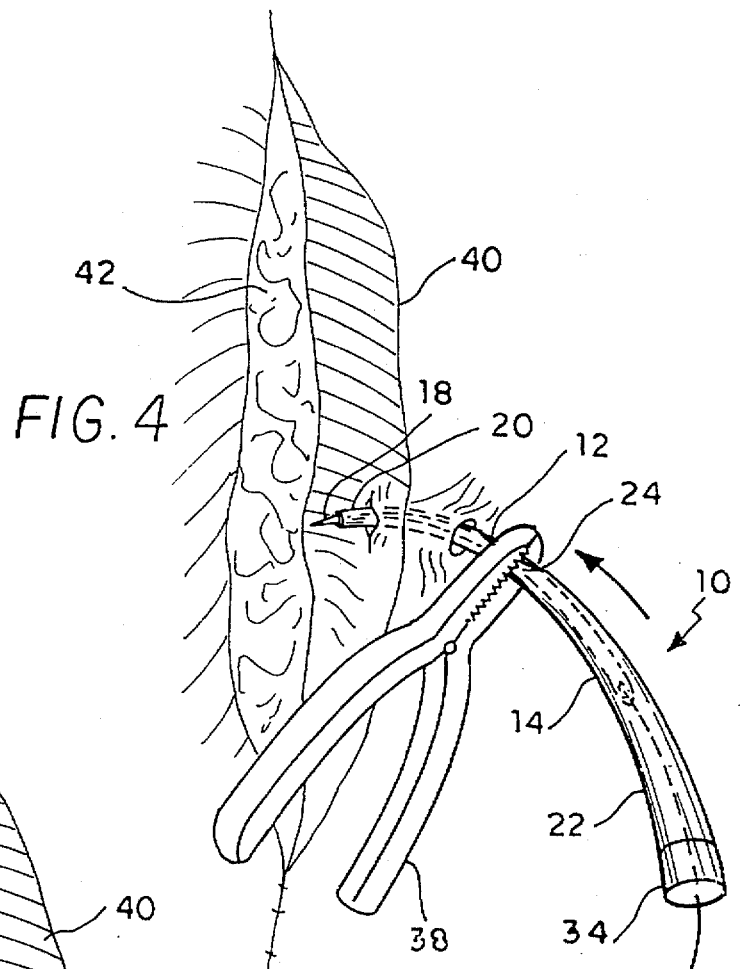
FIG. 4 is an environmental, perspective view of the puncture-proof suturing needle assembly of the present invention in the open state, inserted through tissue to be sutured.
Figure 5:
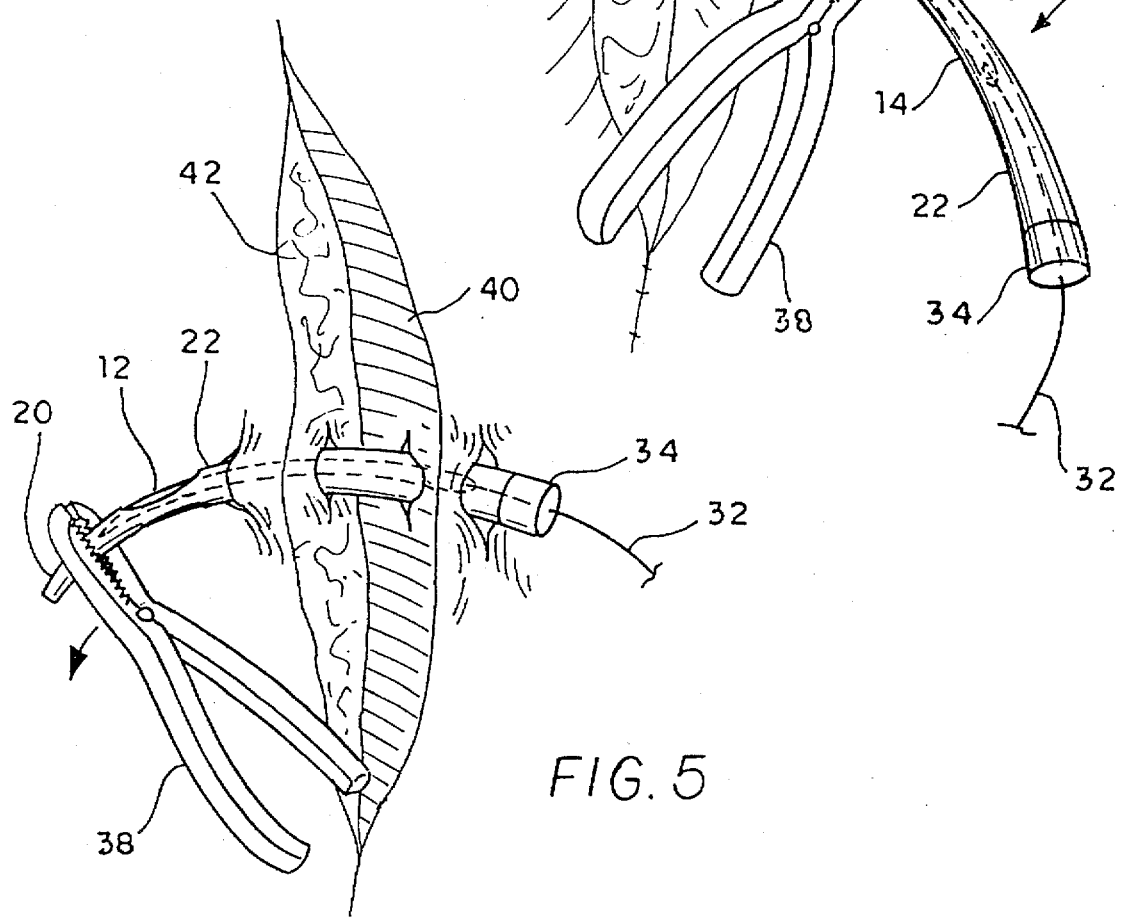
FIG. 5 is an environmental, perspective view of the puncture-proof suturing needle assembly of the present invention in a closed stated, while pulled through the tissue to be sutured.

FIG. 4 and FIG. 5 illustrate the use of suturing needle assembly 10 during surgery. In FIG. 4, a surgeon employs a driver 38, of well known design (such as a hemostat clamp), to manipulate suturing needle assembly 10. Specifically, the opposing jaws of driver 38 grasp flanges 24 and the exposed section of surgical needle 12 proximate thereto. The surgeon can then direct suturing needle assembly 10. With needle tip 18 exposed, to puncture the two sections of patient biological tissue 40, 42 to be sutured together.

Upon extending section 20 through the apertures in tissue sections 40, 42, the surgeon disengages the opposing jaws of driver 38 from flanges 24 and the exposed section of surgical needle 12 proximate thereto. The surgeon then grasps section 20 with the opposing jaws of driver 38, and pulls the remaining portion of suturing needle assembly 10, including section 22, suture guide 34 and suturing medium 32, through the apertures in tissue sections 40, 42. By engaging only section 20 of casing 14, the surgeon frees surgical needle 12 therefrom, so that it slidably recesses proximately into section 22 when suturing needle assembly 10 is pulled completely through the apertures in tissue sections 40, 42. The "drag" of suturing medium 32 facilitates the displacement of surgical needle 12 within casing 14. In this orientation, needle tip 18 is safely sheathed within section 22, to prevent accidental self-puncture, as shown in FIG. 5. When preparing to make a second suture, the surgeon inverts suturing needle assembly 10 to allow surgical needle 12 to return to its position at distal section 20, whereby needle tip 18 is exposed for further penetration of patient biological tissue.

It is to be understood that the present invention is not limited to the sole embodiment described above, but encompasses any and all embodiments within the scope of the following claims.

I claim:

1. A puncture-proof suturing needle assembly comprising:

a surgical needle having a distal end with a sharp tip and a proximate end for securing a suturing medium to said surgical needle;

a casing closely sheathing said surgical needle and allowing freely slidable movement therein, said casing having a distal end and a proximate end, said distal end being tapered to a reduced diameter from said proximate end, said proximate end defining a first aperture for receiving the surgical needle therethrough and said distal end defining a second aperture for limiting protrusion of said sharp tip, said casing dimensioned in length to substantially exceed the length of said surgical needle; and a suture guide for removably plugging said first aperture, said suture guide defining an eye hole for threading of said suturing medium therethrough.

2. The puncture-proof suturing needle assembly according to claim 1, wherein said casing is integrally defined by a distal section and a proximate section and a pair of diametrically opposed flanges connecting said distal section to said proximate section, said flanges, said distal section and said proximate section together defining a pair of diametrically opposed openings positioned along said casing to expose said surgical needle when said sharp tip extends through said second aperture at the fullest protrusion of said tip and to fully occlude said tip from appearing in said openings when said proximate end of said needle is nearest said first aperture.

3. The puncture-proof suturing needle assembly according to claim 1, wherein said proximate section is beveled approaching and terminating with said second aperture for eliminating discontinuities along the surface of said suturing needle assembly.

4. The puncture-proof suturing needle assembly according to claim 1, said casing being substantially frusto-conical.

5. The puncture-proof suturing needle assembly according to claim 1, said suture guide being a substantial cylinder, said eye hole positioned substantially concentrically on said cylinder and dimensioned to prevent passage of said needle, said suture guide made of a material suitable for crimping.

6. A suturing needle casing for use with a surgical needle having a distal end with a sharp tip and a proximate end for securing a suturing medium to said surgical needle, said suturing needle casing comprising:

a casing closely sheathing the surgical needle and allowing freely slidable movement therein, said casing having a distal end and a proximate end, said casing integrally defining a distal section and a proximate section and a pair of diametrically opposed flanges connecting said distal section to said proximate section, said distal end of said distal section being tapered to a reduced diameter, said proximate end of said proximate section defining a first aperture for receiving the surgical needle therethrough and said distal end of said defining a second aperture for limiting protrusion of the sharp tip, said casing dimensioned in length to substantially exceed the length of the surgical needle;

wherein said flanges, said distal section and said proximate section together define a pair of diametrically opposed openings positioned along said casing to expose said surgical needle when said sharp tip extends through said second aperture at the fullest protrusion of said tip and to fully occlude said tip from appearing in said openings when said proximate end of said needle is nearest said first aperture; and, a suture guide for removably plugging said first aperture, said suture guide defining an eye hole for threading of the suturing medium therethrough.

7. The suturing needle casing according to claim 6, wherein said proximate section is beveled approaching and terminating with said second aperture for eliminating discontinuities along the surface of said suturing needle assembly.

8. A surgical suturing method comprising:

preparing a suturing needle assembly comprising:

a surgical needle, the surgical needle having a sharp tip at its distal end and a proximate end for securing a suturing medium to the surgical needle;

a substantially frusto-conical casing for sheathing the needle, the casing having distal and proximate ends defining a first aperture and second aperture respectively, the first aperture dimensioned to allow insertion of the surgical needletherethrough and the distal end tapering to define the second aperture of a reduced diameter, the second aperture accommodating and limiting protrusion of the sharp tip;

a suture guide defining an eye hole through which suturing medium is threaded, and the suture guide insertably plugging the first aperture;

the casing further comprising distal and proximate sections and a pair of diametrically opposed flanges, the flanges integrally connecting the proximate part of the distal section and the distal part of the proximate section, the distal and proximate sections and the flanges defining a pair of diametrically opposed openings through which the surgical needle is exposed when the sharp tip extends through the aperture defined by the distal end of the casing, and the edges of the casing disposed proximate to the surgical needle being beveled to eliminate discontinuities along the surface of the suturing needle assembly; and, the casing containing the surgical needle, so that the distal section tapers to form a snug seal with the tip and the proximate section engages the needle relatively loosely, to better facilitate the sliding displacement thereof;

grasping the suturing needle assembly between the opposing jaws of a surgical driving tool at the flanges and the exposed section of the surgical needle proximate thereto;

directing the suturing needle assembly, with the needle tip exposed, to puncture two opposing sections of patient biological tissue to be sutured together;

extending the distal section through the apertures in the opposing patient biological tissue sections;

disengaging the opposing jaws of the surgical driving tool from the flanges and the exposed section of the surgical needle proximate thereto;

grasping the suturing needle assembly between the opposing jaws of the surgical driving tool at the distal section; and, pulling the remaining portion of the suturing needle assembly through the apertures in the patient biological tissue sections, whereby the surgical needle slidably recesses into the proximate section, thereby safely protecting the needle tip therein, to prevent accidental self-puncture; and, inverting the suturing needle assembly to allow the surgical needle to return to its position at the distal section, thereby exposing the needle tip for further penetration of patient biological tissue.

* * * * *